US012611373B2

(12) United States Patent
Copeland et al.

(10) Patent No.: US 12,611,373 B2
(45) Date of Patent: Apr. 28, 2026

(54) SKINCARE COMPOSITION AND PROCESS FOR CREATING SULFORAPHANE

(71) Applicants: Amber Copeland, Lawrence, KS (US); Kearsti Conner, Eudora, KS (US)

(72) Inventors: Amber Copeland, Lawrence, KS (US); Kearsti Conner, Eudora, KS (US)

( * ) Notice: Subject to any disclaimer, the term of this patent is extended or adjusted under 35 U.S.C. 154(b) by 550 days.

(21) Appl. No.: 18/148,756

(22) Filed: Dec. 30, 2022

(65) Prior Publication Data

US 2023/0210760 A1     Jul. 6, 2023

Related U.S. Application Data

(60) Provisional application No. 63/358,437, filed on Jul. 5, 2022, provisional application No. 63/295,867, filed on Jan. 1, 2022.

(51) Int. Cl.

| | |
|---|---|
| *A61K 8/02* | (2006.01) |
| *A61K 8/34* | (2006.01) |
| *A61K 8/67* | (2006.01) |
| *A61K 8/9789* | (2017.01) |
| *A61Q 19/00* | (2006.01) |

(52) U.S. Cl.
CPC ............ *A61K 8/9789* (2017.08); *A61K 8/022* (2013.01); *A61K 8/345* (2013.01); *A61K 8/676* (2013.01); *A61K 8/678* (2013.01); *A61Q 19/00*
(2013.01); *A61K 2800/84* (2013.01); *A61K 2800/882* (2013.01); *A61K 2800/884* (2013.01)

(58) Field of Classification Search
None
See application file for complete search history.

(56) References Cited

U.S. PATENT DOCUMENTS

| | | | | | |
|---|---|---|---|---|---|
| 2,844,476 | A | * | 7/1958 | Rivoche | ................. A23B 7/022 426/388 |
| 6,436,450 | B1 | * | 8/2002 | Omary | .................... A23L 19/01 424/755 |

FOREIGN PATENT DOCUMENTS

| | | | | | |
|---|---|---|---|---|---|
| EP | | 2213280 A1 | * | 8/2010 | ............. A23L 19/01 |
| WO | WO-2018235805 A1 | | * | 12/2018 | ............. A23L 19/07 |

* cited by examiner

*Primary Examiner* — Melissa S Mercier
(74) *Attorney, Agent, or Firm* — Avek IP, LLC

(57)     ABSTRACT

A skincare composition includes a substance having a predetermined amount of one or more cruciferous vegetables, the predetermined amount of the one or more cruciferous vegetables including stabilized glucoraphanin and active myrosinase in a stable state; exposing the substance to a liquid activator causes a chemical reaction between the stabilized glucoraphanin and the active myrosinase to create sulforaphane in an active product; and applying the activated product to a skin surface allows the sulforaphane to act upon the skin surface.

19 Claims, 4 Drawing Sheets

10

SKINCARE COMPOSITION AND PROCESS FOR CREATING SULFORAPHANE

CROSS-REFERENCE TO RELATED APPLICATIONS

This application claims priority to U.S. Provisional Application No. 63/295,867, filed Jan. 1, 2022, and U.S. Provisional Application No. 63/358,437, filed Jul. 5, 2022, both of which are incorporated by reference in their entirety herein.

BACKGROUND OF THE INVENTION

1. Field

The disclosure relates generally to the fields of cosmetics and skincare. More specifically, the disclosure relates to a skincare composition and process for the creation of sulforaphane as a biproduct of by combining two separate components.

2. Description of the Related Art

Cosmetics and skincare products are well known in the art. Many skincare products incorporate one or more antioxidant and/or anti-inflammatory agents, which help to protect skin against environmental conditions, such as sun damage and pollution. For example, European Patent Publication No. EP3069710A1 to Bell describes a cosmetic composition including one or more antioxidant plant polyphenolic agents. Further, U.S. Pat. No. 5,358,752A to Evans discloses a skin care composition which contains a phenolic diterpene compound for antioxidant effects.

SUMMARY

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages will be apparent from the following detailed description of the embodiments and the accompanying drawing figures.

Embodiments of the present disclosure include a skincare composition comprising a powdered substance having a predetermined amount of one or more powdered cruciferous vegetables, the predetermined amount of the one or more cruciferous vegetables including stabilized glucoraphanin and active myrosinase in a stable state; wherein exposing the powdered substance to a liquid activator causes a chemical reaction between the stabilized glucoraphanin and the active myrosinase to create sulforaphane in an active product; and wherein applying the activated product to a skin surface allows the sulforaphane to act upon the skin surface.

BRIEF DESCRIPTION OF THE DRAWING FIGURES

Embodiments of the invention are described in detail below with reference to the attached drawing figures, wherein.

Figure 1:
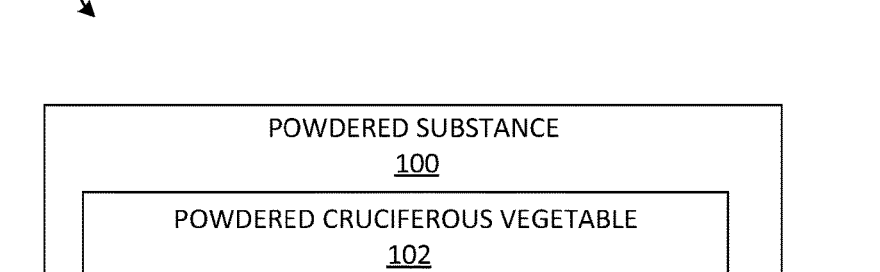
FIG. 1 is a block diagram of an embodiment of a skincare composition in accordance with the present disclosure.
Figure 1:
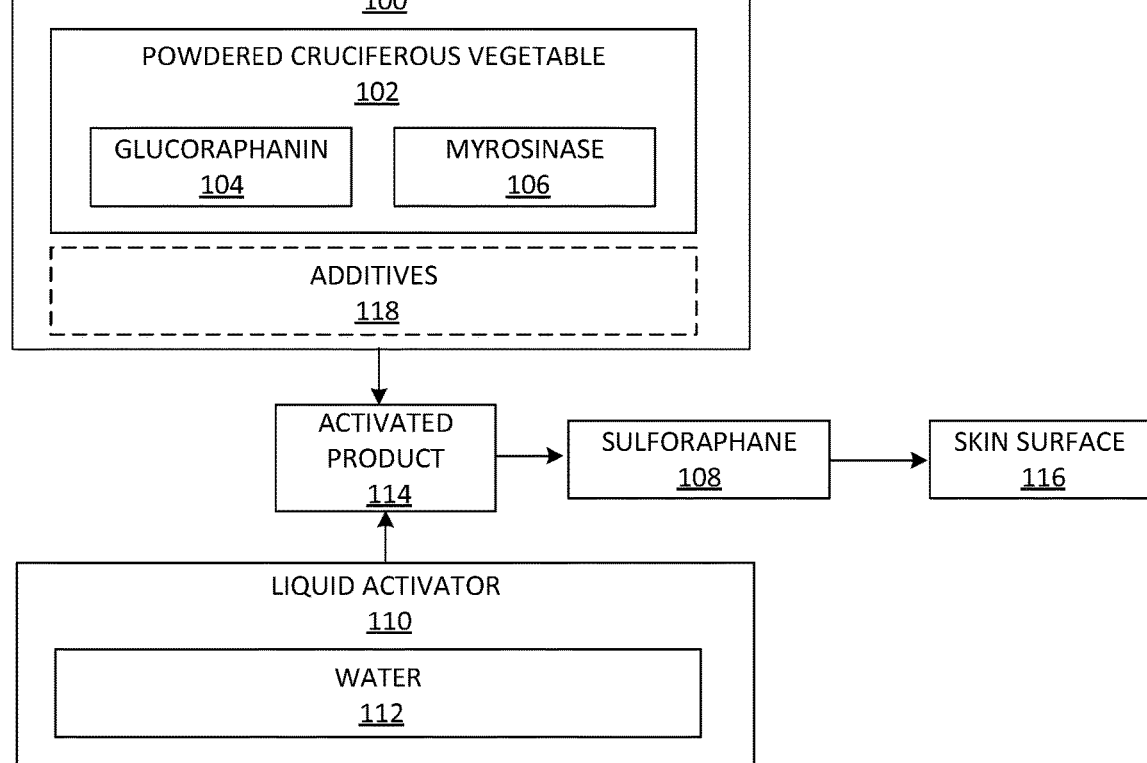

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

Skincare and cosmetic compositions provide numerous benefits to a user. For example, many skincare compositions aim to improve the overall condition of the skin, such as through use of antioxidant properties, antiaging properties, or other skin improving properties. Antioxidants fight signs of aging and improve skin appearances by helping the skin repair itself.

Isothiocyanates are naturally occurring compounds belonging to various plants, particularly to cruciferous vegetables and are understood to contain anticarcinogenic and antioxidant properties. Sulforaphane is a potent isothiocyanate that has been subject to much research and is considered the most, or one of the most, potent naturally occurring dietary activators of the genetic pathway NrF2 which regulates over 200 different genes, many of which are antioxidant and anti-inflammatory genes and genes that inactivate harmful compounds that human skin can be exposed to daily.

Studies show that glucoraphanin is known as a potential sulforaphane producer when activated with exposure to myrosinase, a naturally occurring enzyme. Myrosinase works by catalyzing the hydrolysis of glucoraphanin into sulforaphane.

The high bioavailability of sulforaphane makes it easily accepted by human skin, and there are many studies showing the benefits of sulforaphane consumption by the human body in a variety of ways. There has, however, been a lack of sulforaphane use in skin care and cosmetics due to the rapid and sensitive chemical response and expenditure of the glucoraphanin and myrosinase to external environmental triggers and fast sulforaphane depletion due to rapid insta- bility.

The present invention provides for a shelf stable pow- dered substance, having glucoraphanin and myrosinase in a stable form, wherein exposure to a liquid activator allows for the myrosinase to catalyze the hydrolysis of glucoraphanin into sulforaphane such that the sulforaphane can act upon a skin surface. At a high level, a topical product is created using two separately maintained components, which will ultimately be combined to create sulforaphane for a variety of applications.

In FIG. 1, a block diagram depicts an embodiment of a skincare composition 10 in accordance with the present disclosure. The composition 10 comprises a powdered sub- stance 100 composed at least in part by an amount of one or more powdered cruciferous vegetables 102, which naturally includes glucoraphanin 104 and myrosinase 106 in a stable form. In embodiments, the one or more powdered crucifer- ous vegetables 102 are harvested and dried, such as through lyophilization.

The harvesting and drying of cruciferous vegetables (e.g., the freeze drying of broccoli sprouts, broccoli seeds, kale, cauliflower, mustard seeds, etc.) has continuously been tested to provide the one or more powdered cruciferous vegetables 102 with high levels of glucoraphanin 104, the precursor to sulforaphane 108, and the active enzyme myro- sinase 106. These two remain stable as housemates in the powdered substance 100 until introduced with a liquid activator 110 which starts the chemical process of producing sulforaphane 108.

In embodiments, the liquid activator 110 includes at least an amount of water 112, and in some embodiments is only water 112, which when allowed to act upon the powdered substance 100 allows for the myrosinase 106 to act upon the glucoraphanin 104, beginning the chemical reaction to pro- duce sulforaphane 108. Only upon combination of the liquid activator 110 and the powdered substance 100 will the glucoraphanin 104 and myrosinase 106 blend to provide an activated product 114 with active sulforaphane 108. The sulforaphane 108 can then act directly on the skin surface 116 immediately before degrading of the sulforaphane 108 reduces the potency and effectiveness of the antiaging and antioxidant properties.

In embodiments, one or more additives 118 may be combined with the one or more powdered cruciferous veg- etable 102. Other embodiments will include 100% powdered broccoli sprouts, or another selected cruciferous vegetable.

In embodiments, the liquid activator 110 is water 112 and may be applied to a user's skin, e.g. their face, prior to applying the powdered substance 100. For example, the user may wet their face with water and then apply the powdered substance 100 directly to their face, thereby creating the activated product 144 on their face.

In other embodiments, the liquid activator 100 is water 112 added to the powdered substance 100 to create the activated product 114 before being applied to the user's skin. For example, the user may place an amount of the powdered substance 100 on their hands, in a mixing container, or otherwise, add an amount of water 112, and combine the two into the activated product 114 before then applying the activated product 114 to their skin.

And yet in other embodiments, the liquid activator 110 is moisture naturally occurring on a user's skin such that when the user applies the powdered substance 100, the naturally occurring moisture causes activation.

In any embodiment, it should be appreciated that the powdered substance 100 is exposed to the liquid activator 110 either immediately prior to skin application, or simul- taneously with skin application. This ensures minimal deg- radation of the sulforaphane 108.

Figure 2:
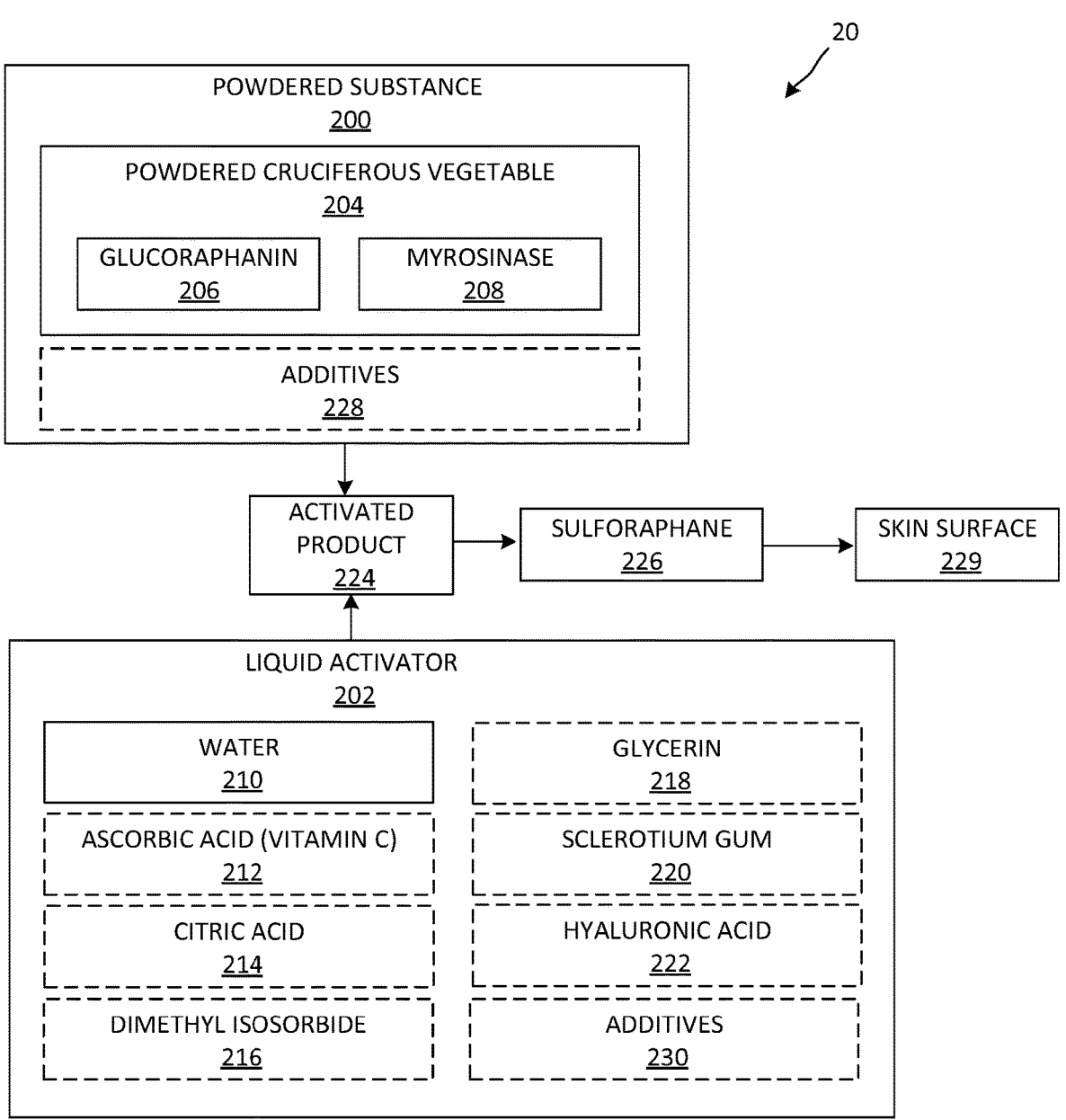
FIG. 2 is a block diagram of an alternative embodiment of a skincare composition in accordance with the present disclosure.

In FIG. 2, another block diagram depicts a second embodiment of a skincare composition 20. Composition 20 comprises a powdered substance 200 and a liquid activator 202. In embodiments, the powdered substance 200 is com- posed at least in part by an amount of one or more powdered cruciferous vegetables 204, which naturally includes gluc- oraphanin 206 and myrosinase 208 in a stable form. In embodiments, the one or more powdered cruciferous veg- etables 204 are harvested and dried, such as through lyo- philization.

Liquid activator 202, in embodiments, may include a plurality of ingredients, including but not limited to, water 210, ascorbic acid 212, citric acid 214, dimethyl isosorbide 216, glycerin 218, sclerotium gum 220, hyaluronic acid 222, and other additives 230. As an example, one embodiment of liquid activator 202 may comprise 65% by weight of deion- ized water; 15% by weight ascorbic acid; 10% by weight citric acid; 5% by weight dimethyl isosorbide; 2% by weight sclerotium gum; and 1% by weight hyaluronic acid.

In embodiments, the liquid activator 202 and the pow- dered substance 200 are provided as a set, wherein the liquid activator 202 is contained in a separate container from the powdered substance 200 and the user is directed to combine the two to create an activated product 224, such that sul- foraphane 226 is created to act upon the skin surface 229.

In embodiments, SanBroc™ Broccoli Seed or other like products could be used to create the powdered cruciferous vegetable 204. In more specific embodiments, the substance extracted from the cruciferous vegetable extract may contain 13% Glucoraphanin and myrosinase.

As with composition 10, the powdered substance 200 of composition 20 may further include one or more additives 228. For example, the one or more additives 118, 228 may include an optional sulforaphane compatible carrier/solvent. The carrier, in embodiments, can be useful in allowing permeation of released hydrophobic sulforaphane into a mammalian body part (e.g., skin or scalp) after the activating liquid 110, 202 has triggered the chemical reaction between the glucoraphanin 206 and myrosinase 208.

In embodiments, the solvent could be a glycol ester solvent, ethoxydiglycol or any other like skin-absorption assisting carrier. For example, in embodiments, 1,3 propane- diol, 1,2 propanediol, a glycerin, a polyethylene glycol, or some other like carrier might be included for the purpose of establishing solubility and permeation into the skin. In other embodiments, oils or other suitable carriers might be used.

Another optional additive 118, 228 may include one or more additional antioxidant components. The antioxidant component, in embodiments, is included for the purpose of avoiding oxidation and thus, establishes product stability. Antioxidants used might include one or more of: mixed tocopherols, Vitamin E, Vitamin C, L ascorbic acid, ascorbyl-6-palmitate, and magnesium ascorbyl phosphate. In embodiments, mixed tocopherols are advantageous to include because they help stabilize the product by avoiding oxidation. Other oxidation stablizers might be used instead, or in addition to mixed tocopherols. L-ascorbic acid might be included for the purpose of increasing sulforaphane production. Alternatively, other sulforaphane production enhancing antioxidants might be used in addition to or instead of the L-ascorbic acid.

In terms of proportion by volume, the formulation of the powdered substance 100, 200 might, in embodiment, be composed of the powdered cruciferous vegetable 102, 204 alone. In more specific embodiments, however, the product might include both the powdered cruciferous vegetable 102, 204 and the one or more additives 118, 228 as discussed above, such as the sulforaphane compatible carrier/solvent. In yet other embodiments, the powdered cruciferous vegetable 102, 204 might be combined with the one or more additives 118, 228 in the form of antioxidants without the carrier/solvent. Where the formulation includes the powdered cruciferous vegetable 102, 204, a sulforaphane compatible carrier/solvent, and an antioxidant, each component might be included in the ranges shown below:

powdered cruciferous vegetable: 0.05-100%
   sulforaphane compatible carrier/solvent: 0-99.95%
   Antioxidants: 0-20%

In more specific embodiments, the powdered cruciferous vegetable, a sulforaphane compatible carrier/solvent, and an antioxidant could be included in these more specific ranges:

Cruciferous-vegetable-derived product: 2-20%
   sulforaphane compatible carrier/solvent: 80-98%
   Antioxidants: 0.0005-10%

In even more specific embodiments, the powdered cruciferous vegetable, a sulforaphane compatible carrier/solvent, and an antioxidant could be included in these more specific ranges:

powdered cruciferous vegetable: 2-15%
   sulforaphane compatible carrier/solvent: 85-95%
   Antioxidants: 0.005-2%

In a more specific embodiment, the powdered cruciferous vegetable, a solvent, and an antioxidant were at the following levels:

powdered cruciferous vegetable: About 10%
   Solvent: About 89%
   Antioxidants: About 1%

As discussed, a second component of the composition 10, 20 of the present disclosure is a separately-maintained, water-based activator. In embodiments, the liquid activator 110 is substantially water, and can be substantially pure water. It is known that other substances, e.g., aqueous solutions such as aloe water, or other aqueous topical solutions might be used.

Figure 3:
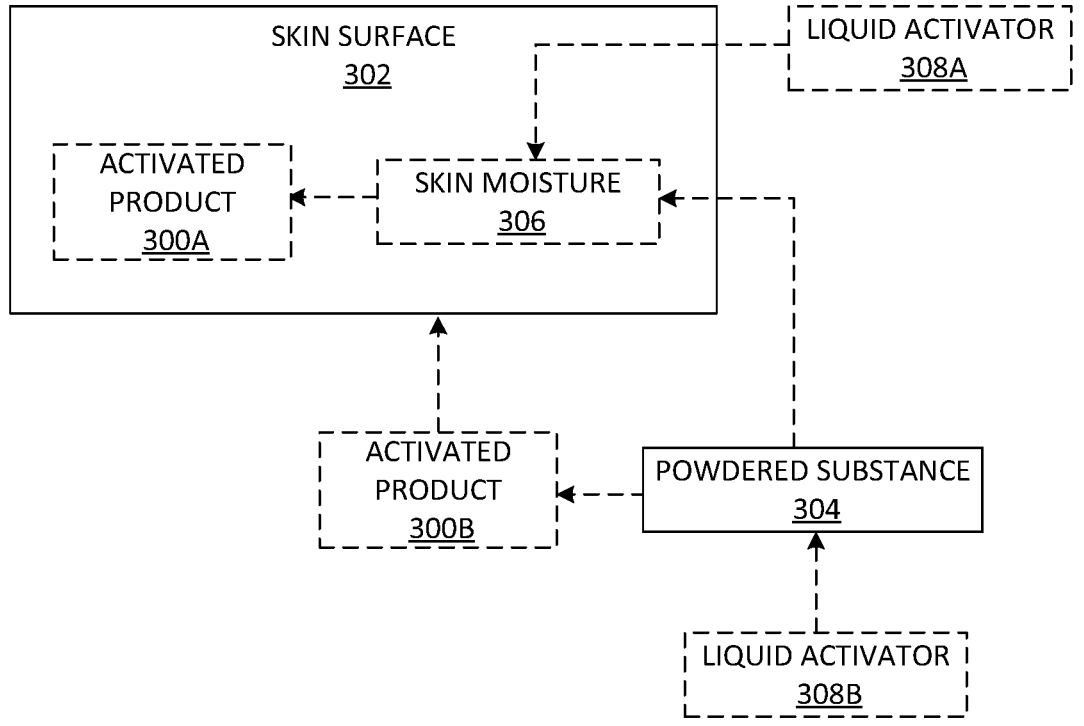
FIG. 3 is a block diagram of a plurality of processes of using the skincare composition of the present disclosure.

In FIG. 3, a block diagram depicts embodiments of use of the composition 10, 20 of the present disclosure. As shown, the ultimate result is application of the activated product 300A-B on a user's skin surface 302. The skin surface 302 may be a user's face or other areas of their body. As discussed, the activated product 300A-B includes sulforaphane to provide benefits to the skin surface, such as antiaging and antioxidant properties.

In some embodiments, the powdered substance 304 is applied directly to the skin surface 302, wherein the powered substance 304 mixes with skin moisture 306, such as moisture naturally occurring on the skin and including enough water or other aqueous product to activate the ingredients of the powdered substance 304, resulting in the activated product 300A.

In other embodiments, a liquid activator 308A is applied to the skin surface 302 to create the skin moisture 306 prior to the addition of the powdered substance 304. The liquid activator 308A may be water, or another liquid activator, such as discussed above, which provides enough moisture to cause activation of the powered substance 304 into the activated product 300A.

In yet other embodiments, the powered substance 304 is directly mixed with a liquid activator 308B, thereby creating an activated product 300B prior to being placed on the skin surface 302. For example, the user may mix water or another liquid activator into the powered substance 304 in their hands or in a separate container, and then proceed to applying to the skin surface 302.

It should be understood that the powered substance and the liquid activator are separately maintained components that are mixed, either immediately before, or during actual use of the composition (e.g., upon application to the skin, etc.). The term "immediately" as used herein should not be considered limited to any particular timing without limitation. The term does imply that the two components are mixed after initial manufacture on the site of an application.

In embodiments, the powdered substance and liquid activator could be presented as a cosmetic product in the form of a two-compartment dispenser. In this sort of embodiment, the dispenser might have a first containing system devoted to the powered substance, and a second containing system devoted to the liquid activator.

Alternatively, the two components can be exposed to one another apart from any particular dispensing arrangement. For example, the powered substance could be presented as the product with the direction to a user to expose the powdered substance to water or some other activation component.

Figure 4:
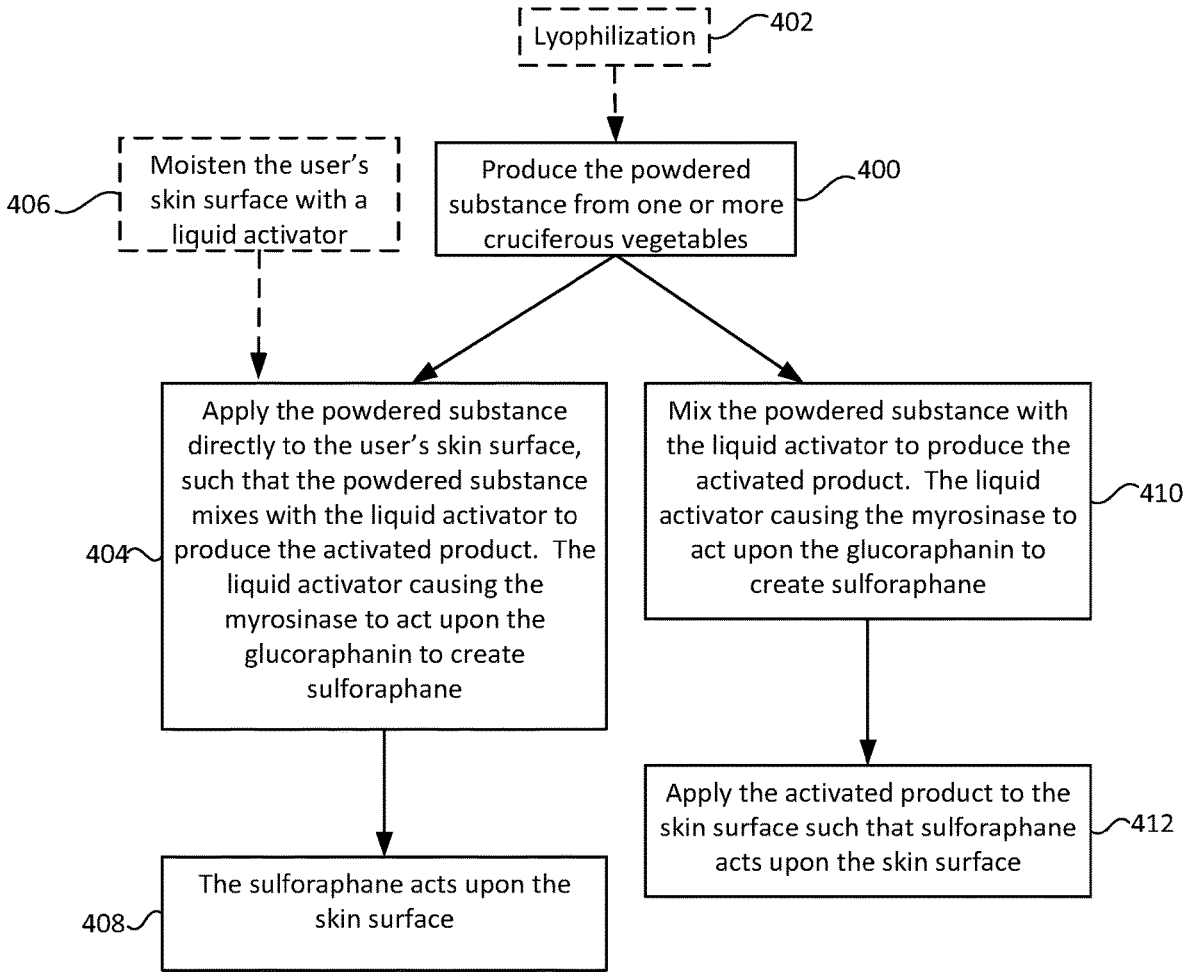
FIG. 4 is a flowchart of a process of creating sulforaphane and using sulforaphane in accordance with the present disclosure.

In FIG. 4, a flowchart further summarizes processes for creating sulforaphane contemplated in the present disclosure. As shown, the powdered substance is produced, wherein the powdered substance is composed at least in part by one or more powdered cruciferous vegetables, shown in box 400. In embodiments, the one or more powdered cruciferous vegetables are created through lyophilization, as shown in box 402. Those skilled in the art would readily understand alternative means of drying and powdering one or more cruciferous vegetables.

In some embodiments, the powdered substance is applied directly to the user's skin surface such that the powdered substance mixes with the liquid activator to produce the activated product, as shown with box 404. It should be appreciated that in some applications, the liquid activator is merely moisture present on the skin surface, as would be naturally occurring. However, in other embodiments, a user may apply a liquid activator to their skin prior to the addition of the powdered substance, as shown with box 406. As the liquid activator causes the myrosinase to act upon the glucoraphanin, sulforaphane is created to act upon the skin surface, as shown with box 408.

In alternative applications, the powdered substance may be combined with a liquid activator prior to being applied to the skin, as shown with box 410. For example, a user may add an amount of water or other liquid activator to the powdered substance, either in their hands or in a secondary container, wherein the liquid activator begins the chemical reaction such that when the activated product is applied to the skin surface, sulforaphane is present to act thereon, as shown with box 412.

The ratio by volume of the powdered substance versus the liquid activator (measured before being combined) should be such that, at a minimum, some of the myrosinase and glucoraphanin in the powdered substance is activated to produce the chemical reaction for the isothiocyanate sulforaphane in the needed potency and bioavailability. Ideally, the amount of the liquid activator should be sufficient by volume to substantially activate all of the myrosinase and glucoraphanin. In embodiments, the amount of the liquid activator could modestly exceed the amount required for full myrosinase and glucoraphanin reaction.

Referring back to FIGS. 1-3, as discussed, the powered substance 100, 200 may include one or more additives 118, 228. Further, the liquid activator 202, in embodiments, may further include additional additives 230.

In embodiments, the various additives 118, 228, 230 may include one or more thickeners present in amounts up to about 10% by weight. E.g., a thickener such as hydroxyethylcellulose in an amount of about 2% has been included with embodiments above without creating significant detriment to sulforaphane extraction. As is known to those skilled in the art, the precise number of thickeners can vary depending upon the desired consistency and thickness of the composition.

Additionally, the various additives 118, 228, 230 may include one or more preservatives to protect against the growth of potentially harmful microorganisms. Preservatives can be included in amounts ranging from about 0.01% to about 2% by weight of the composition.

Additionally, the various additives 118, 228, 230 may include one or more minor ingredients such as fragrances, antifoam agents, opacifiers and colorants. Particularly useful minor ingredients are vitamin E linoleate, sunscreen agent, sodium hyaluronate and aloe vera gel, as well as other botanicals.

For purposes of this invention, the weight ratio of the powdered substance 100, 200 versus the amount of the liquid activator 110, 202 may range from about 10:1 to 1:10. In more specific embodiments, the ratio between the two components can be kept close to 1:1. Regardless, the amount of liquid activator 110, 202 needed will be selected at a level that accomplishes substantial activation of the Glucoraphanin and Myrosinase included in the powdered substance 100, 200. Thus, in embodiments, the level of activator would be maintained to substantially activate, or above. This may be dictated in part by the amount of powdered cruciferous vegetable 102, 204. Additionally, physical properties (e.g., viscosity) of the ultimate product composition might dictate the liquid activator 110, 202 amount.

Example 1

An embodiment was tested wherein the powdered substance 100, 200 included the following formulation:

1,3 propanediol—88.95%
Broccoli Seed Extract—10%
Mixed Tocopherols—1%
L-Ascorbic Acid—0.05%

The broccoli seed extract shown above, more specifically, was SanBroc™ Broccoli Seed Extract which includes 13% Glucoraphanin Plus Myrosinase which is manufactured by Chengdu SanHerb BioScience Co., Ltd. located in Chengdu, China This composition was mixed 1:1 with 100% water.

The measured sulforaphane after mixing was measured at 1.6 mg/g which is the equivalent to 9020 nmol/g. These values showed high levels of sulforaphane production. Previous studies using sulforaphane topically applied 300-800 nmol/g with positive testing results.

Example 2

An alternative formulation was tested, the alternative formulation including:

Distilled Water—to 100%
Broccoli Sprout Powder—3%

Ascorbic Acid—0.05%
Tocopherol Acetate—1%

The broccoli seed extract shown above, more specifically, Organic Broccoli Sprout Powder—USA Sprouted & Freeze-dried was sold by KOYAH.

The measured sulforaphane after HPLC testing was measured at 0.0545/mg/g which is equivalent to 307 nmol/g. The use of water in the composition was shown to attribute to the extreme deterioration of the sulforaphane produced unstable for commercial use.

The composition 10, 20 according to the present disclosure might have numerous uses. For example, the product could be presented as an indirect and/or a direct antioxidant upon application to the skin (human or other mammalian). The composition 10, 20 is also useful as a topically-applied UV-protection agent. Additionally, studies suggest that sulforaphane absorption by the body may prevent cancer. The product might also be presented as an anti-inflammatory product, an anti-aging product, a testosterone blocking hair-loss prevention topical product, or numerous other topical uses.

Many different arrangements of the various components depicted, as well as components not shown, are possible without departing from the spirit and scope of what is claimed herein. Embodiments have been described with the intent to be illustrative rather than restrictive. Alternative embodiments will become apparent to those skilled in the art that do not depart from what is disclosed. A skilled artisan may develop alternative means of implementing the aforementioned improvements without departing from what is claimed.

It will be understood that certain features and subcombinations are of utility and may be employed without reference to other features and subcombinations and are contemplated within the scope of the claims. Not all steps listed in the various figures need be carried out in the specific order described.

The invention claimed is:

1. A skincare composition comprising:
   a substance having a predetermined amount of one or more cruciferous vegetables, the predetermined amount of the one or more cruciferous vegetables including stabilized glucoraphanin and active myrosinase in a stable state;
   wherein exposing the substance to a liquid activator causes a chemical reaction between the stabilized glucoraphanin and the active myrosinase to create sulforaphane in an active product;
   wherein the liquid activator is a second substance separate from the substance; and
   wherein applying the activated product to a skin surface allows the sulforaphane to act upon the skin surface.

2. The skincare composition of claim 1, wherein the substance is powdered.

3. The skincare composition of claim 1, wherein the one or more cruciferous vegetables is composed of dried and powdered broccoli sprouts.

4. The skincare composition of claim 1, wherein one or more cruciferous vegetables are lyophilized to create the amount of one or more cruciferous vegetables in the substance.

5. The skincare composition of claim 1, wherein the substance comprises:
   0.05-100% percentage by weight of the one or more cruciferous vegetables;
   0-99.95% percentage by weight of a sulforaphane compatible carrier; and 0-20% percentage by weight of one or more antioxidant additives.

6. The skincare composition of claim 1, wherein the substance comprises:

2-20% percentage by weight of the one or more cruciferous vegetables;

80-98% percentage by weight of a sulforaphane compatible carrier; and 0.0005-10% percentage by weight of one or more antioxidant additives.

7. The skincare composition of claim 1, wherein the substance comprises:

2-15% percentage by weight of the one or more cruciferous vegetables;

85-95% percentage by weight of a sulforaphane compatible carrier; and 0.005-2% percentage by weight of one or more antioxidant additives.

8. The skincare composition of claim 1, wherein the liquid activator comprises approximately 65% water.

9. The skincare composition of claim 1, wherein the powdered substance is stored in a first container and the liquid activator is stored in a second container.

10. The skincare composition of claim 1, wherein the liquid activator comprises about:

65% by weight of deionized water;

15% by weight ascorbic acid;

10% by weight citric acid;

5% by weight Dimethyl Isosorbide;

2% by weight sclerotium gum; and

1% by weight hyaluronic acid.

11. The skincare composition of claim 1, further comprising one or more additives, the one or more additives selected from a group consisting of:

one or more carriers for improving permeation of the sulforaphane through the skin surface; and one or more antioxidant components for improving stability of the activated product.

12. The skincare composition of claim 1, wherein the one or more cruciferous vegetables is selected from a group consisting of dried broccoli sprouts, dried broccoli seeds, dried kale, dried cauliflower, and dried mustard seeds.

13. The skincare composition of claim 1, wherein the liquid activator comprises water.

14. A skincare composition comprising:

a substance having a predetermined amount of one or more cruciferous vegetables, the predetermined amount of the one or more cruciferous vegetables including stabilized glucoraphanin and active myrosinase in a stable state, the substance further comprising:

2-20% percentage by weight of the one or more cruciferous vegetables;

80-98% percentage by weight of a sulforaphane compatible carrier; and 0.0005-10% percentage by weight of one or more antioxidant additives;

wherein exposing the substance to a liquid activator causes a chemical reaction between the stabilized glucoraphanin and the active myrosinase to create sulforaphane in an active product; and wherein applying the activated product to a skin surface allows the sulforaphane to act upon the skin surface.

15. The skincare composition of claim 14, wherein the one or more cruciferous vegetables is selected from a group consisting of dried broccoli sprouts, dried broccoli seeds, dried kale, dried cauliflower, and dried mustard seeds.

16. The skincare composition of claim 14, wherein the one or more cruciferous vegetables is composed of dried and powdered broccoli sprouts.

17. The skincare composition of claim 14, wherein one or more cruciferous vegetables are lyophilized to create the amount of one or more cruciferous vegetables in the substance.

18. The skincare composition of claim 14, further comprising the liquid activator as a second substance contained separately from the substance.

19. The skincare composition of claim 14, wherein the liquid activator comprises at least 65% water.

* * * * *